United States Patent [19]

Jacquet et al.

[11] 4,426,375

[45] Jan. 17, 1984

[54] COSMETIC COMPOSITIONS FOR THE HAIR AND THE SKIN BASED ON POLYMERS WHICH CONTAIN AMINO GROUPS AND RECURRING UNITS HAVING A CYCLIC STRUCTURE

[75] Inventors: Bernard Jacquet, Antony; Christos Papantoniou, Montmorency; Jean Mondet, Sevran, all of France

[73] Assignee: L'Oreal, Paris, France

[21] Appl. No.: 276,193

[22] Filed: Jun. 22, 1981

Related U.S. Application Data

[62] Division of Ser. No. 944,140, Sep. 20, 1978, Pat. No. 4,287,720.

[30] Foreign Application Priority Data

Sep. 23, 1977 [LU] Luxembourg .................... 78170

[51] Int. Cl.³ .................... A61K 7/06; A61K 7/09
[52] U.S. Cl. .................... 424/70; 8/405; 8/406; 424/47; 424/63; 424/71; 424/72; 424/357; 424/358
[58] Field of Search .................... 424/70

[56] References Cited

U.S. PATENT DOCUMENTS

| | | | |
|---|---|---|---|
| 2,926,161 | 2/1960 | Butler et al. | 526/310 |
| 3,288,770 | 11/1966 | Butler | 260/88.3 |
| 3,412,019 | 11/1968 | Hoover et al. | 526/292 |
| 3,544,318 | 12/1970 | Boothe et al. | 526/310 X |
| 3,743,715 | 7/1973 | Viout et al. | 424/47 |
| 3,790,537 | 2/1974 | Panzer et al. | 526/310 |
| 3,833,531 | 9/1974 | Keim | 526/46 |
| 3,910,862 | 10/1975 | Barabas et al. | 424/71 X |
| 3,912,808 | 10/1975 | Sokol | 424/71 |
| 3,986,825 | 10/1976 | Sokol | 424/71 |
| 3,996,146 | 12/1976 | Tarasov et al. | 424/70 |

FOREIGN PATENT DOCUMENTS

| | | | |
|---|---|---|---|
| 49-69789 | 5/1974 | Japan | 526/310 |
| 51-57793 | 5/1976 | Japan | 526/310 |
| 905831 | 9/1962 | United Kingdom | 526/310 |

*Primary Examiner*—Dale R. Ore
*Attorney, Agent, or Firm*—Cushman, Darby & Cushman

[57] ABSTRACT

Cosmetic compositions for the hair and skin are described which are characterized in that they contain a polymer which comprises recurring units having the general formula

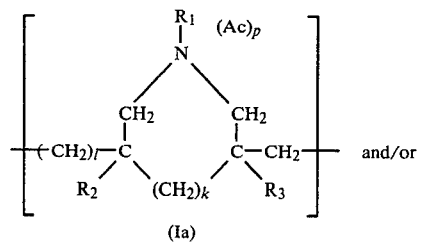

(Ia)

and/or

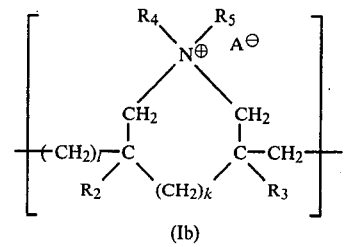

(Ib)

in which:
  k is 0 or 1, and l=1 if k=0, or l=0 if k=1,
  p=0 or 1 and the radicals $R_1$ to $R_5$ represent various specified organic radicals.

8 Claims, No Drawings

COSMETIC COMPOSITIONS FOR THE HAIR AND THE SKIN BASED ON POLYMERS WHICH CONTAIN AMINO GROUPS AND RECURRING UNITS HAVING A CYCLIC STRUCTURE

This is a division of application Ser. No. 944,140 filed Sept. 20, 1978, now U.S. Pat. No. 4,287,172.

The present invention relates to polymers which contain amine groups and comprise units having a cyclic structure, cosmetic compositions containing them and to their use for the care of the hair and the skin.

For some years, it has been proposed to use, for the care of the hair and of the skin, certain polymers which contain amine groups which are either tertiary or quaternary i.e. ammonium groups.

It was in fact found that these polymers had a certain affinity for the keratin of the hair and of the skin and hence made it possible to avoid sensations of dryness and roughness of the hair and of the skin. However, it was also found that these polymers exhibited a degree of incompatibility in some cosmetic compositions, which therefore considerably limited their use.

Furthermore, it was found that the affinity of these polymers was insufficiently durable and hence it was necessary to repeat the applications very frequently in order to impart to the skin and to the hair a natural appearance which is visually pleasing and pleasant to the touch.

It has now been discovered, according to the present invention, that by using a new class of polymers which contain amine groups and comprise units having a cyclic structure, it is possible, on the one hand, to obtain a large variety of formulations without encountering the disadvantages found with the previous polymers and, on the other hand, to achieve a durable effect in view of the greater affinity of the polymers used, according to the invention, towards the keratin of the hair and of the skin.

This invention provides, a cosmetic composition for the care of the hair and of the skin, which contains, in a suitable cosmetic vehicle, at least one polymer which comprises units having a cyclic structure corresponding to the following formulae:

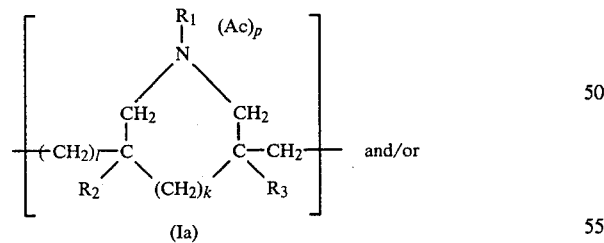

(Ia)

and/or

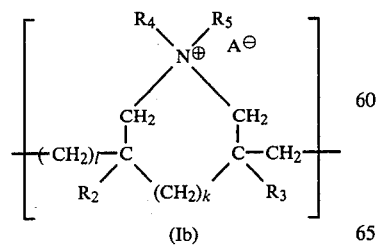

(Ib)

in which:
k is 0 or 1, and l=1 if k=0, or l=0 if k=1,
p=0 or 1,
$R_2$ and $R_3$, which may be identical or different, represent a hydrogen atom or a methyl radical,
$R_1$ represents a radical selected from the group comprising:
(i) —$CH_2$—$COOR_6$, with $R_6$ representing an alkyl radical having from 1 to 3 carbon atoms,

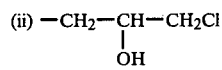

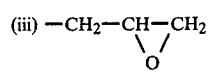

(iv) —$(CH_2)_n$—CN, n being equal to 1 or 2,
(v) —$COR_7$, with $R_7$ representing an alkyl radical having from 1 to 3 carbon atoms, a —$CCl_3$ radical, a —$CH_2Cl$ radical, a phenyl radical or a radical of the formula:

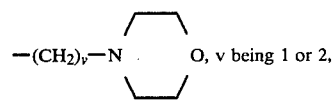

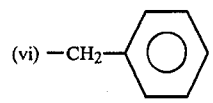

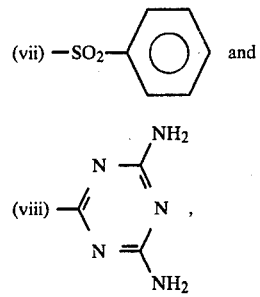

$R_4$ represents a hydrogen atom or a radical selected from the group comprising:
(a) —$(CH_2)_m$—$CH_3$, m being 0 to 21 inclusive,
(b) —$(CH_2)_q$—$OC_2H_5$, q being 1 or 2,
(c) —$CH_2COOR_6$, $R_6$ having the same meaning as above and

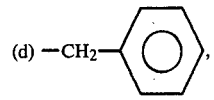

$R_5$ represents a radical selected from the group comprising:
(1) —$(CH_2)_q$—$OC_2H_5$, q being 1 or 2,
(2) —$CH_2$—$COOR_6$, $R_6$ having the same meaning as above,

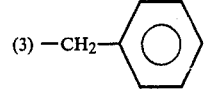

-continued (4) —CH₂—CH—CH₂Cl
　　　　　|
　　　　　OH (5) —CH₂—CH—CH₂
　　　　　\\ /
　　　　　　O (6) —(CH₂)ₙ—CN, n being equal to 1 or 2, (7) —COR₇, R₇ having the same meaning as above, (8) —SO₂—C₆H₅ (phenyl)

(9) 
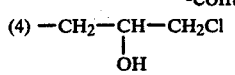
(triazine with two NH₂ groups)

(10) —CH₂—CH=CH₂

(11) —CH₂—CH₂—O—CH=CH₂ and

(12) —(CH₂)₆—N⁺(r')(r")(r''') A'⁻ r', r" and r''', which may be identical or different, represent an alkyl radical having from 1 to 4 carbon atoms, A and A', which may be identical or different, represent Cl, Br, I or OSO₃CH₃ and Ac (if p=1) represents an inorganic or organic acid and preferably hydrochloric acid, hydrobromic acid, nitric acid, acetic acid, butyric acid or lactic acid.

According to a first preferred embodiment of the invention the polymers have an exclusively polycyclic structure and are either homopolymers or copolymers which can be represented by the following general formula:

$$\left[\begin{array}{c}\text{(Ia)}\end{array}\right]_x \left[\begin{array}{c}\text{(Ib)}\end{array}\right]_y \quad \text{(II)}$$

(Ia) structure with $R_1$, N, $(Ac)_p$, CH₂, (CH₂)$_l$—C—$R_2$, (CH₂)$_k$, C—CH₂—$R_3$ (Ib) structure with $R_4$, $R_5$, N⁺, $A^\ominus$, CH₂, (CH₂)$_l$—C—$R_2$, (CH₂)$_k$, C—CH₂—$R_3$ in which:
$R_1$, $R_2$, $R_3$, $R_4$, $R_5$, Ac, l, k, p and A have the same meanings as above,
x+y corresponds to 100 mol % and one of x and y can be equal to 0.

According to a second preferred embodiment of the invention, the polymers are copolymers which can be represented by the following general formula:

$$\left[\begin{array}{c}\text{(Ia)}\end{array}\right]_x \left[\begin{array}{c}\text{(Ib)}\end{array}\right]_y \left[M_1\right]_z \quad \text{(III)}$$

in which:
$R_1$, $R_2$, $R_3$, $R_4$, $R_5$, Ac, l, k, p and A have the same meanings as above, and
$M_1$ represents a unit of at least one homopolymerisable monomer selected from the group consisting of:
(i) the monomers of the following formula:

$$\text{(IV)}$$

(structure with $R_8$, N, $(Ac)_p$, CH₂, CH₂, $R_2$—C, C—$R_3$, CH₂, CH₂)

in which:
$R_2$, $R_3$, Ac and p have the same meanings as above and
$R_8$ represents a —CH₂—CH₂OH radical or a —(CH₂)ₙ—CH₃ radical, n being 0 to 11 inclusive,
(ii) the monomers of the following formula:

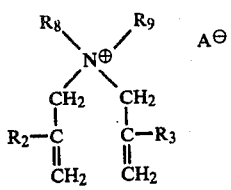

in which:

$R_2$, $R_3$, $R_8$ and A have the same meanings as above and $R_9$ represents a methyl radical, (iii) the monomers of the following formula:

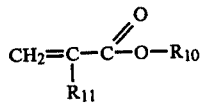

in which:

$R_{11}$ represents a hydrogen atom or a methyl radical and $R_{10}$ represents a hydrogen atom or a radical selected from the group comprising a linear or branched alkyl radical having from 1 to 18 carbon atoms, an alkyl radical having from 1 to 3 carbon atoms which is substituted by at least one alkoxy radical having from 1 to 4 carbon atoms, a radical of the formula:

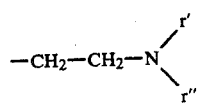

and a radical of the formula:

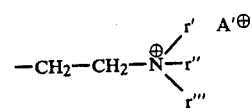

in which:

r', r'', r''' and A' have the same meanings as above, (iv) the monomers of the following formula:

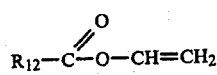

in which:

$R_{12}$ represents a linear or branched alkyl radical having from 1 to 18 carbon atoms, (v) the monomers of the following formula:

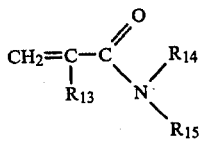

in which:

$R_{13}$ represents either a hydrogen atom or a methyl radical and $R_{14}$ and $R_{15}$, which may be identical or different, represent a hydrogen atom, or a linear or branched alkyl radical having from 1 to 4 carbon atoms which may be substituted by 1, 2 or 3 hydroxyl groups, and (vi) N-vinylpyrrolidone, x+y represents from 5 to 95 mol %, one of x and y can be 0 and z represents from 5 to 95 mol %.

According to a third preferred embodiment of the invention the polymers are copolymers which can be represented by the following general formula:

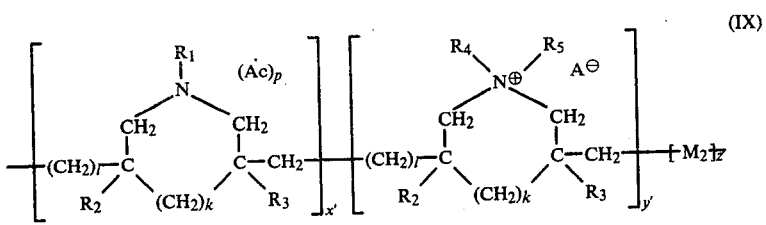

in which:

$R_1$, $R_2$, $R_3$, $R_4$, $R_5$, Ac, l, k, p and A have the same meanings as above, $M_2$ represents a unit of at least one non-homopolymerisable monomer selected from the group comprising:

(a) the monomers of the following formula:

in which:

$R_{16}$ represents a linear or branched alkyl radical having from 1 to 17 carbon atoms, (b) the monomers of the following formula:

$$R_{17}-O-CH=CH_2 \quad (XI)$$

in which $R_{17}$ represents an alkyl radical having from 1 to 18 carbon atoms, and (c) the monomers of the following formula:

$$R_{18}-CH=CH_2 \quad (XII)$$

in which:

$R_{18}$ represents an alkyl radical having from 1 to 18 carbon atoms, x'+y' represents from 50 to 95 mol %, and one of x' and y' can be 0 and z' represents from 5 to 50 mol %.

The polymers which can be used according to this invention exhibit the peculiarity of being soluble both in water and in alcohols, especially ethanol and isopropanol.

These polymers usually have a molecular weight of 2,000 to 500,000 and preferably 4,000 to 75,000.

The units (Ia) of the polymers can be derived, by cyclopolymerisation, from a salified diallylamine having the following formula:

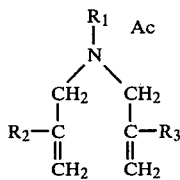
(XIII)

in which:

$R_1$, $R_2$ and $R_3$ have the same meanings as above and Ac is an inorganic or organic acid, and the units (Ib) of the polymers can be derived, by cyclopolymerisation, from a quaternary ammonium salt, and especially a chloride or bromide, having the following formula:

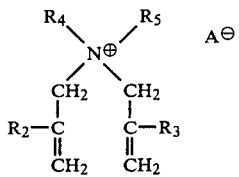
(XIV)

in which:

$R_2$, $R_3$, $R_4$, $R_5$ and A have the same meanings as above.

In fact, during polymerisation the compounds of the formulae (XIII) and (XIV) cyclise to give the cyclic units (Ia) and (Ib) respectively, which possess either five or six members in the cyclic structure.

Furthermore, if the radical $R_5$ above represents a radical which carries a polymerisable double bond, the latter can also participate in the cyclisation and in that case units having a bicyclic structure are obtained, as is the case, for example, if the radical $R_5$ represents an allyl radical.

Amongst the diallylamines of the formula (XIII) which give the units (Ia), there may in particular be mentioned the hydrochlorides, hydrobromides, hydroiodides, nitrates, acetates, butyrates and lactates of N-trichloroacetyl-diallylamine, N-chloroacetyl-diallylamine, N-acetonitrile-diallylamine, N-acetyl-diallylamine, N-propionitrile-diallylamine, N-propionyl-diallylamine and N-benzenesulphonyl-diallylamine, N-ethyl acetate diallylamine, N-methyl acetate diallylamine and the hydrochloride, hydrobromide, nitrate, acetate, butyrate and lactate of diallylmelamine.

Amongst the ammonium salts of the formula (XIV) which give the units (Ib) there may in particular be mentioned the methyl-(2-etheneoxy-eth-1-yl)-diallylammonium, methyl-(2-ethoxy-eth-1-yl)-diallylammonium, methyl-(2-phenoxy-eth-1-yl)-diallylammonium, methyl-(2-methoxy-eth-1-yl)-diallylammonium, methyl-methoxycarbonylmethylene-diallylammonium and methylethoxycarbonylmethylene-diallylammonium chlorides, bromides, iodides and methyl-sulphates, the butyl-(2-etheneoxy-eth-1-yl)-diallylammonium, octyl-(2-etheneoxy-eth-1-yl)-diallylammonium, dodecyl-(2-etheneoxy-eth-1-yl)-diallylammonium, benzyl-(2-etheneoxy-eth-1-yl)-diallylammonium, ethoxycarbonylmethylene-(2-etheneoxy-eth-1-yl)-diallylammonium, ethoxycarbonylmethylene-(2-ethoxy-eth-1-yl)-diallylammonium, octyl-ethoxycarbonylmethylene-diallylammonium, butyl-benzyldiallylammonium, butyl-ethoxycarbonylmethylene-diallylammonium, methyl-triallylammonium, butyl-triallylammonium, octyl-triallylammonium, decyl-triallylammonium, dodecyltriallylammonium, ethyl-triallylammonium and benzyl-triallylammonium chlorides, bromides and iodides, N,N-diallyl-N,N',N',N'-tetramethyl-hexyl-1,6-diammonium dibromide and N,N-diallyl-N,N',N'-trimethyl-N'-butyl-hexyl-1,6-diammonium dibromide.

Amongst the unsaturated monomers which give the units $M_1$ of the copolymers of the formula (III) there may in particular be mentioned:

(i) Amongst the monomers of the formula (IV): the N-methyl-diallylamine, N-ethyl-diallylamine, N-butyl-diallylamine, N-octyl-diallylamine and N-dodecyl-diallylamine hydrochlorides, hydrobromides, hydroiodides, acetates, butyrates and lactates.

(ii) Amongst the monomers of the formula (V): the dimethyl-diallylammonium, methyl-butyl-diallylammonium, ethyl-butyl-diallylammonium, methyl-octyl-diallylammonium, methyl-decyl-diallylammonium and methyl-dodecyl-diallylammonium chlorides, bromides and iodides.

(iii) Amongst the monomers of the formula (VI): acrylic acid, methacrylic acid and methyl, ethyl, propyl, isopropyl, butyl, isobutyl, s-butyl, 2-methyl-butyl, 3-methyl-butyl, 2-ethyl-butyl, amyl; hexyl, 3-methyl-hexyl, 3-ethyl-hexyl, 2-ethyl-hexyl, 2-methoxy-ethyl, 2-ethoxyethyl and lauryl acrylates and methacrylates, the 2-N,N-dialkylamino-ethyl acrylates and methacrylates and in particular 2-N,N-dimethylamino-ethyl and 2-N,N-diethylaminoethyl acrylates and methacrylates, optionally quaternised with dimethyl sulphate, ethyl bromide or any other quaternising agent, as well as (2-methacryloyloxy-eth-1-yl)-trimethyl-ammonium methyl-sulphate.

(iv) Amongst the monomers of the formula (VII): vinyl acetate, vinyl propionate, vinyl butyrate and vinyl stearate.

(v) Amongst the monomers of the formula (VII): acrylamide, methacrylamide, N-methylacrylamide, N-tertiarybutylacrylamide, N-hydroxymethylacrylamide, N-(1,1-dimethyl-2-hydroxy-eth-1-yl)-acrylamide and the N,N-dimethyl-, N,N-diethyl-, N,N-dibutyl- and N,N-diisobutyl-acrylamides and -methacrylamides.

Amongst the unsaturated monomers which give the units $M_2$ of the copolymers of the formula (IX) there may in particular be mentioned:

(a) Amongst the monomers of the formula (X): allyl acetate, allyl hexanoate, allyl dodecanoate and allyl octadecanoate.

(b) Amongst the monomers of the formula (XI): methyl vinyl ether, ethyl vinyl ether, isobutyl vinyl ether, dodecyl vinyl ether and octadecyl vinyl ether.

(c) Amongst the monomers of the formula (XII): but-1-ene, oct-1-ene, dodec-1-ene and octadec-1-ene.

It will, of course, be understood in formulae (II), (III) and (IX), the units (Ia) and (Ib) and M units are not necessarily in blocks; generally the polymers are random copolymers, x, y, z, x', y', and z' merely representing the molar proportion of the units in question in the polymer.

The copolymers (and homopolymers), can be obtained by copolymerisation in emulsion or in solution in water or an organic liquid such as ethanol, methanol, benzene, toluene or xylene.

Conventional polymerisation catalyst can be used, for example hydrogen peroxide, benzoyl peroxide or azo-bis-isobutyronitrile, but preferably t-butyl peroxypivalate or t-butyl hydroperoxide.

The polymerisation reaction can also be initiated by irradiation or by oxidation-reduction systems such as the hydro peroxide/ferrous chloride or ammonium persulphate/ferrous chloride systems.

The polymerisation is in general carried out at a temperature of 30° to 150° C. and preferably 60° to 90° C.

If it is desired to obtain polymers in which the units (Ia) are in the form of free amines, the polymers obtained in a salified form can be treated with a base such as sodium hydroxide, at ambient temperature.

The cosmetic compositions according to the invention, containing the specified polymers can be in various forms.

The cosmetic compositions according to the invention can contain the polymers either as the principal active ingredient or as an additive i.e. additional ingredient.

Furthermore, the compositions in general contain at least one adjuvant usually employed in cosmetic compositions.

The cosmetic compositions can be in the form of, for example, aqueous, alcoholic or aqueous-alcoholic solutions (the alcohol being, in particular, a lower alkanol such as ethanol or isopropanol), or in the form of creams, gels or emulsions, or in the form of aerosols which contain a propellant.

The adjuvants generally present in the cosmetic compositions according to the invention may be, for example, perfumes, dyestuffs, preservatives, sequestering agents, or thickeners.

It should be noted that the cosmetic compositions according to the invention are either ready-to-use compositions or concentrates which can be diluted before use.

The cosmetic compositions according to the invention are thus not limited to a particular polymer concentration range. In general, the polymer concentration is from 0.01 to 15% by weight and preferably from 0.1 to 10% by weight.

If the specified polymers are applied to the head of hair either by themselves or together with other active substances when carrying out a treatment such as a shampoo, a dyeing operation or a wave-set, they significantly improve the characteristics of the hair and in particular restore its suppleness and an attractive sheen.

Furthermore, they assist the treatment and facilitate the combing-out of the wet hair. In contrast to the previous polymers, they do not make the dry hair heavy and hence make it easy to produce bulky hairstyles. Furthermore, they make an efficient contribution to eliminating the shortcomings of hair which has been sensitised by chemical treatments or deteriorated by the atmosphere, by exposure to the sun or by bathing in the sea.

The polymers used in the compositions according to the invention are of particular value when used as pre-treatment agents, especially with an anionic and/or non-ionic shampoo, or prior to an oxidation dyeing treatment which is itself followed by an anionic and/or non-ionic shampoo.

After such treatment, the hair is particularly easy to comb out and is very soft to the touch.

The polymers can also be used as pre-treatment agents in other hair treatment operations, for example in permanent waving.

The cosmetic compositions for the hair are suitably in the form of aqueous, alcoholic or aqueous-alchoholic solutions (the alcohol preferably being either ethanol or isopropanol) or in the form of creams, gels or emulsions, or in the form of sprays. In this latter case, the compositions are packaged in an aerosol container which contains a propellant such as nitrogen, nitrous oxide, carbon dioxide or a fluorochlorohydrocarbon such as those known by the name "Freon", or mixtures of such propellants.

The adjuvants generally present in the cosmetic compositions for hair according to the invention, include perfumes, dyestuffs, preservatives, sequestering agents, thickeners and emulsifiers as well as hair resins.

The cosmetic compositions for hair, according to the invention, thus include, in particular:

(a) Treatment compositions which contain at least one polymer, in aqueous or aqueous-alcoholic solution, as the active ingredient.

The polymer content is generally 0.01 to 15% by weight and preferably 0.1 to 8% by weight.

The pH of these lotions in near the neutral point and can, for example, be from 6 to 8.

If necessary, the pH can be brought to the desired value by adding either an acid such as citric acid or a base, especially an alkanolamine such as monoethanolamine or triethanolamine.

In order to treat the hair with such a lotion, the lotion is applied to the wetted hair and is allowed to act for, say, 3 to 15 minutes, and the hair is then rinsed.

The hair can then be wave-set if desired.

(b) Shampoos which contain at least one polymer and a cationic, non-ionic or anionic detergent.

Suitable cationic detergents include long-chain quaternary ammonium compounds, esters of fatty acids and aminoalcohols, and polyether-amines.

Suitable non-ionic detergents include esters of polyols and of sugars, condensation products of ethylene oxide with fatty compounds, with long-chain alkylphenols, with long-chain mercaptans or with long-chain amides, and polyethers of polyhydroxylic fatty alcohols.

Suitable anionic detergents include the alkali metal salts, ammonium salts, amine salts or aminoalcohol salts of fatty acids such as oleic acid, ricinoleic acid, copra oil acids or hydrogenated copra oil acids, the alkali metal salts, ammonium salts or aminoalcohol salts of fatty alcohol-sulphates, especially of $C_{12}$–$C_{14}$ fatty alcohols and of $C_{16}$ fatty alcohols, the alkali metal salts, magnesium salts, ammonium salts or aminoalcohol salts of oxyethylenenated fatty alcohol-sulphates, the condensation products of fatty acids with isethionates, taurine, methyltaurine and sarcosine, the alkylbenzenesulphonates, especially with $C_{12}$-alkyl, the alkylaryl-polyether-sulphates and the monoglyceride-sulphates.

All these detergents, as well as numerous others which can be used, are well known and are described in the literature.

These compositions in the form of shampoos can also contain various adjuvants such as perfumes, dyestuffs, preservatives, thickeners, foam stabilisers, softeners, or one or more cosmetic resins.

In these shampoos, the detergent concentration is generally from 5 to 50% by weight and the concentration of polymer of the formula (I) is generally from 0.01 to 15%, and preferably from 0.1 to 5% by weight.

(c) Wavesetting lotions, especially for sensitised hair, characterised in that they contain at least one polymer as defined above, in aqueous, alcoholic or aqueous-alcoholic solution.

These compositions in the form of wavesetting lotions can furthermore contain another cosmetic resin.

The concentration of the specified polymer in these wavesetting lotions is generally from 0.1 to 5%, and preferably 0.2 to 3%, by weight.

The pH of these wavesetting lotions is generally from 3 to 9 and preferably from 4.5 to 7.5.

(d) Hair dyeing compositions, characterised in that they contain at least one polymer, a colorant and a vehicle. The vehicle preferably consists of a cream.

The concentration of polymer is these dyeing compositions is generally from 0.5 to 15% by weight and preferably from 0.5 to 10% by weight.

In the case of an oxidation dyeing treatment, the dyeing composition can be packaged in two parts, the second part being hydrogen peroxide, the two parts being mixed at the time of use.

(e) Hair lacquers, characterised in that they contain an alcoholic or aqueous-alcoholic solution of at least one polymer, optionally together with another resin, this solution being placed in an aerosol container and mixed with a liquefied propellant under pressure.

For example, an excellent aerosol lacquer according to the invention can be obtained by mixing at least one of the specified polymers with an anhydrous aliphatic alcohol such as ethanol or isopropanol and with a propellant or a mixture of such propellants, such as those enumerated above.

In these compositions in the form of hair lacquers, the concentration of polymers is in general from 0.5 to 3% by weight.

Of course, as in the case of the preceding compositions, it is possible to add to these lacquers various ingredients such as dyestuffs or plasticisers (f) Pre-treatment compositions, in particular in the form of aqueous or aqueous-alcoholic solutions, optionally in the form of aerosols, or in the form of creams or gels, these pre-treatment compositions being intended to be applied to the hair before a shampoo, especially before an anionic or non-ionic shampoo, before an oxidation dyeing treatment followed by an anionic and/or non-ionic shampoo, or before a permanent waving treatment.

In these pre-treatment compositions, the polymer constitutes the active ingredient and its concentration is generally from 0.1 to 15% and in particular from 0.2 to 8% by weight.

The pH of these compositions is near the neutral point and is generally from 3 to 9, especially 6 to 8.

These pre-treatment compositions can contain various adjuvants usually employed in cosmetic compositions for hair, such as plasticisers, perfumes and dyestuffs.

As indicated above, the cosmetic compositions according to the invention can also be used, in the form of a beauty mask or of a make-up product, for the treatment of the skin.

In effect, these compositions make it possible to facilitate the hydration of the skin and thus to prevent its drying-out. Furthermore, an excellent softness to the touch can be imparted to the skin by means of these compositions.

Such cosmetic compositions according to the invention are preferably in the form of creams, gels, emulsions or aqueous, alcoholic or aqueous-alcoholic solutions.

The polymer concentration in these compositions for the skin is generally from 0.1 to 15% by weight and preferably from 0.2 to 6% by weight.

The adjuvants which may be present in these cosmetic compositions include perfumes, dyestuffs, preservatives, thickeners, sequestering agents, emulsifiers and sunlight filters.

These compositions for the skin are, in particular, creams or treatment lotions for the hands or for the face, or anti-sunburn creams, tinted creams, make-up remover milks, foam bath liquids or deodorant compositions.

These compositions can be prepared by conventional methods.

For example, in order to obtain a cream, an aqueous phase in which the polymer and optionally other ingredients or adjuvants are dissolved, and an oily phase, can be emulsified.

The oily phase can consist of for example, paraffin oil, vaseline oil, sweet almond oil, avocado oil, olive oil and esters of fatty acids such as glyceryl monostearate, ethyl palmitate, isopropyl palmitate and alkyl myristates, such as propyl myristate, butyl myristate or cetyl myristate. It is furthermore possible to add fatty alcohols such as cetyl alcohol or waxes such as beeswax.

The polymers can be present in the cosmetic compositions for the skin either as an additive or as a principal active ingredient.

The following Examples further illustrate the present invention.

EXAMPLES OF THE PREPARATION OF THE COPOLYMERS

EXAMPLE 1

100 g (0.44 mol) of methyl-triallylammonium bromide, 200 g of ethanol and 5 g of azo-bis-isobutyronitrile are introduced into a 1 liter flask equipped with a mechanical stirrer and a nitrogen inlet.

The reaction mixture is heated to 70° C. and kept at this temperature for 72 hours, whilst stirring. The solution is allowed to cool and is then poured dropwise into acetonitrile. The polymer which has precipitated is filtered off and dried at 40° C. under reduced pressure.

Yield: 40%.

EXAMPLE 2

Following the procedure of Example 1, 20 g (0.08 mol) of methyl-(2-ethenoxy-eth-1-yl)-diallylammonium bromide and 80 g (0.345 mol) of methyl-triallylammonium bromide are copolymerised in the presence of 5 g of azo-bis-isobutyronitrile.

After precipitation and drying, the polymer is obtained in a yield of 30%.

Examples of 3 to 49 are summarised in Tables I to IV which follow.

These copolymers were prepared in accordance with the procedure of Example 1, using the precipitation agents or other means of purification indicated in the tables.

For all these Examples, azo-bis-isobutyronitrile was used as the catalyst.

The compositions are expressed in molar fractions.

The symbols used in the tables have the following meanings:
a: water
b: acetone
c: acetonitrile
d: dialysis
e: ethyl acetate
f: 10/90 diethyl ether/acetone
g: crude.

TABLE I

| EXAMPLES | 3 | 4 | 5 | 6 | 7 | 8 | 9 | 10 | 11 | 12 | 13 |
|---|---|---|---|---|---|---|---|---|---|---|---|
| butyl-triallylammonium bromide | 1 | | | | | | | | | | 0.45 |
| octyl-triallylammonium bromide | | 1 | | | | | 0.19 | | | | |
| decyl-triallylammonium bromide | | | 1 | | | | | | | | |
| dodecyl-triallylammonium bromide | | | | 1 | | | | | | | |
| ethyl-triallylammonium bromide | | | | | 1 | | | | | 0.14 | |
| benzyl-triallylammonium bromide | | | | | | 1 | | 0.61 | | | |
| methyl-triallylammonium bromide | | | | | | | | | | 0.51 | |
| dimethyl-diallylammonium bromide | | | | | | | | 0.39 | | | |
| methyl-octyl-diallylammonium bromide | | | | | | | 0.81 | | | | |
| methyl-dodecyl-diallylammonium bromide | | | | | | | | | 0.86 | 0.49 | |
| methyl-decyl-diallylammonium bromide | | | | | | | | | | | 0.55 |
| Precipitant | b | d | a | a | c | d | a | b | d | b | f |
| Yield, % | 47 | 29 | 30 | 44 | 47 | 15 | 36 | 26 | 4 | 32 | 36 |

TABLE II

| EXAMPLES | 14 | 15 | 16 | 17 | 18 | 19 | 20 | 21 | 22 | 23 | 24 | 25 | 26 | 27 |
|---|---|---|---|---|---|---|---|---|---|---|---|---|---|---|
| octyl-triallylammonium bromide | | | | | | 0.31 | | | | | | | | 0.66 |
| decyl-triallylammonium bromide | | | 0.23 | | | | | | | | 0.6 | 0.22 | | |
| dodecyl-triallylammonium bromide | | | | | | | | | | | | | 0.22 | |
| benzyl-triallylammonium bromide | | | | | | | 0.13 | | | | | | | |
| methyl-(2-etheneoxy-eth-1-yl)-diallylammonium bromide | | | | 0.3 | | | | | | | | | | |
| methyl-triallylammonium bromide | 0.37 | 0.51 | | | 0.33 | | | 0.13 | 0.27 | 0.4 | | | | |
| methyl-octyl-diallyl-ammonium bromide | | | | | | | | | | | | | | 0.12 |
| methyl-dodecyl-diallyl-ammonium bromide | | | | | | | 0.08 | | | | | | | |
| methyl-decyl-diallyl-ammonium bromide | | | | | | | | | | | | 0.42 | | |
| butyl-ethyl-diallyl-ammonium bromide | | | 0.77 | | | | | | | | | | | |
| dimethyl-diallylammonium chloride | | 0.49 | | | | | | | | | | | | |
| ethyl-diallylamine hydrochloride | 0.63 | | | | | | | | 0.16 | | | | | |
| N—vinylpyrrolidone | | | | 0.7 | 0.67 | 0.69 | 0.87 | 0.79 | 0.57 | | | | 0.56 | |
| 2-N,N—dimethylamino-eth-1-yl methacrylate | | | | | | | | | | 0.6 | 0.4 | 0.36 | 0.22 | 0.22 |
| Precipitant | b | b | d | b | b | a | b | b | b | g | b | a | b | a |
| Yield, % | 37 | 57 | 26 | 40 | 55 | 99 | 25 | 33 | 58 | 78 | 26 | 28 | 30 | 26 |

TABLE III

| EXAMPLES | 28 | 29 | 30 | 31 | 32 | 33 | 34 | 35 | 36 | 37 | 38 | 39 | 40 |
|---|---|---|---|---|---|---|---|---|---|---|---|---|---|
| methyl-triallylammonium bromide | 0.55 | | | 0.3 | 0.36 | 0.55 | 0.42 | 0.53 | | | | | |
| butyl-triallylammonium bromide | | 0.55 | | | | | | | | 0.17 | | | |
| ethyl-triallylammonium bromide | | | 0.26 | | | | | | | | 0.15 | | |
| dodecyl-triallylammonium bromide | | | | | | | | | | 0.75 | | 0.2 | 0.27 |
| octyl-triallylammonium bromide | | | | | | | | | | | | | |
| benzyl-triallylammonium bromide | | | | | | | | | | | | | |
| α-dodecene | 0.45 | | | | | | | | | | | | |
| allyl acetate | | | 0.45 | | | | | | | | | | |
| vinyl acetate | | | | 0.74 | | | | | | | | | |
| methyl methacrylate | | | | | 0.7 | | | | | | | | |
| N—tertiary butyl-acrylamide | | | | | | 0.64 | | | | 0.83 | | | |
| (2-methacryloyloxy-eth-1-yl)-trimethylammonium methyl-sulphate | | | | | | | 0.45 | | | | 0.25 | | |

TABLE III-continued

| EXAMPLES | 28 | 29 | 30 | 31 | 32 | 33 | 34 | 35 | 36 | 37 | 38 | 39 | 40 |
|---|---|---|---|---|---|---|---|---|---|---|---|---|---|
| hexyl methacrylate | | | | | | | 0.58 | | | | 0.85 | | |
| lauryl methacrylate | | | | | | | | 0.47 | | | | | |
| N—hydroxymethacrylamide | | | | | | | | | | | | 0.8 | |
| (1-(1,1-dimethyl-2-hydroxy-ethyl)-acrylamide | | | | | | | | | | | | | 0.73 |
| Precipitant | b | b | b | a | b | b | a | b | a | b | b | b | b |
| Yield, % | 50 | 26 | 20 | 13 | 58 | 77 | 23 | 28 | 99 | 26 | 60 | 72 | 48 |

TABLE IV

| EXAMPLES | 41 | 42 | 43 | 44 | 45 | 46 | 47 | 48 | 49 |
|---|---|---|---|---|---|---|---|---|---|
| ethyl-triallylammonium bromide | 0.22 | | 0.3 | | | | | | |
| octyl-triallylammonium bromide | | 0.12 | | | | | | | |
| butyl-triallylammonium bromide | | | | 0.32 | | | | | |
| benzyl-triallylammonium bromide | | | | | 0.08 | 0.29 | | | |
| methyl-triallylammonium bromide | | | | | | | 0.12 | 0.28 | 0.77 |
| butyl-ethyl-diallylammonium bromide | 0.22 | | | | | | | | |
| dimethyl-diallylammonium bromide | | | 0.3 | | | | 0.19 | | |
| methyl-dodecyl-diallylammonium bromide | | 0.19 | | | | 0.25 | | | |
| dimethyl-diallylammonium chloride | | | | | | | | 0.41 | |
| N—tertiary-butylacrylamide | 0.56 | | | | 0.57 | | 0.31 | | |
| vinyl acetate | | 0.69 | | | | | | | |
| α-dodecene | | | | 0.4 | | | | | |
| 2-N,N—dimethylamino-eth-1-yl methacrylate | | | | | 0.42 | | | | |
| lauryl methacrylate | | | | 0.26 | | | | | |
| acrylamide | | | | | 0.35 | | 0.38 | | 0.23 |
| N—hydroxymethyl-acrylamide | | | | | | 0.46 | | | |
| (2-methacryloyloxy-eth-1-yl)-trimethylammonium methyl-sulphate | | | | | | | | 0.31 | |
| Precipitant | d | e | d | b | c | b | b | b | b |
| Yield, % | 36 | 52 | 12 | 33 | 46 | 30 | 73 | 66 | 52 |

EXAMPLE 50

Preparation of the copolymer of Example 14 in a non-salified form 10 g of the copolymer prepared according to Example 14 are dissolved in 50 g of water whilst stirring at ambient temperature. 1 N Sodium hydroxide is added to this solution until the pH of the solution is 13. Stirring is continued for 1 hour and the mixture is then dialysed. The polymer is collected in the form of a white powder.

EXAMPLE 51

Following the same procedure as that described in Example 50, the polymer of Example 22 was also obtained in a non-salified form, with a yield of 54%.

EXAMPLES OF COMPOSITIONS

EXAMPLE A

A treatment composition intended to be applied after a shampoo is prepared according to the invention by mixing the following ingredients:
vaseline oil—15 g,
cetyl/stearyl alcohol—2.5 g,
cetyl/stearyl alcohol polyoxyethyleneated with 10 mols of ethylene oxide—2.5 g,
copolymer obtained according to Example 1—1.2 g,
water, q.s.p.—100 g.
The pH of this composition is 4.4.

This composition is applied to the wet hair for a few minutes and the hair is then rinsed. Excellent combing-out of the hair is achieved in this way, and the hair is shiny and easy to style.

In this Example, the polymer obtained according to Example 1 can be replaced by the same amount of one of the polymers prepared according to Examples 2, 3, 10, 14, 15, 17 to 23 and 49.

EXAMPLE B

A wavesetting lotion is prepared, according to the invention, by mixing the following ingredients:
copolymer obtained according to Example 4—1.5 g,
ethyl alcohol—50 g,
perfume—0.1 g,
dyestuff—0.4 g,
water, q.s.p.—100 g.
The pH of this composition is 5.

After application of this lotion, the hair combs out easily and is shiny, springy and free from electrostatic charges.

In this Example, the polymer obtained according to Example 4 can advantageously be replaced by the same amount of one of the polymers prepared according to Examples 5, 6, 8, 19 to 21 and 30 to 37.

EXAMPLE C

A wavesetting lotion is prepared according to the invention by mixing the following ingredients:
copolymer obtained according to Example 12—0.5 g,
quaternary vinylpyrrolidone copolymer of molecular weight 100,000, marketed under the name of "Gafquat 734" by Messrs. General Anilin—0.5 g,
quaternised cellulose sold under the name of "JR 400" by Messrs. Union Carbide—0.3 g,
ethyl alcohol, q.s.p.—15 g,
perfume—0.3 g,
dyestuff—0.2 g,
water, q.s.p.—100 g.
The pH of this composition is adjusted to 8.

This wavesetting lotion, when applied to bleached hair, makes it possible to achieve excellent combing-out of the wet hair. After drying the hair, an excellent waveset is obtained, the hair being soft to the touch, shiny and easy to style.

In this Example, the polymer obtained according to Example 12 can be replaced by the same amount of one of the polymers prepared according to Examples 15, 16, 18 to 21, 39, 41 and 43.

EXAMPLE D

A brushing lotion is prepared according to the invention by mixing the following ingredients:
 copolymer obtained according to Example 26—0.6 g,
 trimethylcetylammonium bromide—0.2 g,
 perfume—0.2 g,
 dyestuff—0.4 g,
 water, q.s.p.—100 g.

The pH of this composition is 6.5.

This lotion is applied to dried natural hair by the brushing technique. The passage of the brush is made easier and the dry hair is soft, shiny and free from electrostatic charges.

In this Example, the polymer obtained according to Example 26 can be replaced by the same amount of one of the polymers obtained according to Examples 28, 29, 44, 47 and 48.

EXAMPLE E

A shampoo is prepared according to the invention by mixing the following ingredients:
 sodium lauryl ether-sulphate (2.2 mols of ethylene oxide)—14 g,
 lauric acid diethanolamide—3 g,
 copolymer obtained according to Example 35—1 g,
 perfume—0.15 g,
 dyestuff—0.2 g,
 water, q.s.p—100 g.

The pH of this composition is adjusted to 7.5 by adding lactic acid.

EXAMPLE F

A pre-shampooing composition is prepared according to the invention by mixing the following ingredients:
 copolymer obtained according to Example 30—1 g,
 trimethylcetylammonium bromide—1 g,
 propylene glycol, q.s.p.—100 g.

The pH of this composition is 7.2.

This product is applied before the shampoo. After leaving it for a few minutes, the hair is rinsed. The combing-out of the wet hair is made easier. After shampooing and wave-setting, the hair is springy and easy to style.

In this Example, the polymer obtained according to Example 30 can be replaced by the same amount of one of the polymers obtained according to Examples 20, 32, 36 and 40.

EXAMPLE G

A hair treatment cream is prepared according to the invention by mixing the following ingredients:
 cetyl/stearyl alcohol oxyethyleneated with 2 mols of ethylene oxide, sold under the name of "BRIJ 72" by Messrs. Atlas—18 g,
 polymer obtained according to Example 7—1 g,
 water, q.s.p.—100 g.

60 to 80 g of this cream are applied to clean, moist and towel-dried hair so as to impregnate and cover the whole of the head of hair.

After waiting for 15 to 20 minutes, the hair is rinsed. The wet hair is soft and easy to comb out. After wavesetting, the hair combs out easily and is silky to the touch.

Furthermore, the hair is glossy and springy and possesses body and bulk.

EXAMPLE H

A dyeing carrier in the form of a cream is prepared according to the invention by mixing the following ingredients:
 cetyl alcohol—18 g,
 ammonium lauryl-sulphate (30% of active material)—12 g,
 stearyl alcohol oxyethyleneated with 15 mols of ethylene oxide—3 g,
 lauryl alcohol—5 g,
 copolymer obtained according to Example 10—3 g,
 ammonia of 22° B strength—12 ml,
 Dyestuff: m-diaminoanisole sulphate—0.048 g,
 resorcinol—0.420 g,
 m-aminophenol base—0.150 g,
 nitro-para-phenylenediamine—0.085 g,
 para-toluylenediamine—0.004 g,
 ethylenediaminetetraacetic acid—1 g,
 sodium bisulphite, d=1.3—1.2 g,
 water, q.s.p.—100 g.

30 g of this formulation are mixed with 45 g of hydrogen peroxide of 20 volumes strength. A thick smooth cream which is pleasant to apply and which adheres well to the hair is obtained.

This cream is applied to the hair by means of a paintbrush and is left for 30 minutes, after which the hair is rinsed.

The hair combs out easily and is silky to the touch.

On 100% white hair, a blond shade is obtained.

In this Example, the polymer obtained according to Example 10 can be replaced by the same amount of one of the polymers prepared according to Examples 10, 12, 41, 43, 50 and 51.

EXAMPLE I

A structuring lotion is prepared according to the invention by mixing the following ingredients at the time of use:
 dimethylolethylenethiourea—1.6 g
 copolymer obtained according to Example 3—1.2 g
 hydrochloric acid, q.s.p. pH=2.7
 water, q.s.p.—100 ml This lotion is applied to the washed and towel-dried hair before wave-setting.

After wave-setting, the hair is shiny, springy and has body and bulk; furthermore the hair is silky and combingout is made easier.

EXAMPLE J

An aerosol lacquer is prepared according to the invention by mixing the following ingredients:
 copolymer obtained according to Example 20—6.5 g
 perfume—0.2 g
 ethanol, q.s.p.—100 g 25 g of this composition are packaged in an aerosol container with 45 g of trichlorofluoromethane and 30 g of dichlorodifluoromethane.

In this way, a film of excellent quality is formed after spraying. The hair is shiny and soft to the touch.

In this Example, the polymer obtained according to Example 20 can be replaced by the same amount of one of the polymers obtained according to Examples 32, 36, 50 and 51.

EXAMPLE K

An aerosol lacquer is prepared according to the invention by mixing the following ingredients:
polymer obtained according to Example 40—5 g
perfume—0.07 g
ethanol, q.s.p.—100 g 93 g of this solution are packaged in an aerosol container with a sufficient amount of carbon dioxide to bring the internal pressure to 8 bars.

As in the preceding Example, excellent lacquering of the hair is achieved by spraying.

The polymer obtained according to Example 40 can advantageously be replaced by the same amount of one of the polymers prepared according to Examples 20, 32 and 36.

EXAMPLE L

A film-forming body milk is prepared according to the invention by mixing the following ingredients;
diethylhexyl adipate—4.8 g
stearic acid—2.9 g,
lanolin alcohol ethoxylated with 5 mols of ethylene oxide—0.5 g,
cetyl alcohol—0.4 g,
glycerol stearate—1 g
triethanolamine—0.95 g,
propylene glycol—4.8 g,
polymer prepared according to Example 21—0.5 g,
preservative—0.2 g,
perfume—0.1 g,
sterile demineralised water, q.s.p.—100 g.

EXAMPLE M

A beauty mask is prepared according to the invention by mixing the following ingredients:
polymer prepared according to Example 12—20 g,
propylene glycol—5 g,
methyl para-hydroxybenzoate (preservative)—0.2 g,
ethanol—15 g,
kaolin—10 g,
titanium oxide—0.5 g,
triethanolamine lauryl-sulphate—6 g,
perfume—0.15 g,
sterile demineralised water, q.s.p.—100 g.

The propylene glycol is dissolved in the preservative solution (comprising the whole of the water+the preservative) at 60° C.

After cooling, the other constituents are incorporated with moderate stirring.

For this Example, the polymer according to Example 12 can be replaced by the same amount of a polymer prepared according to Examples 39, 41, 43, 44 and 48.

EXAMPLE N

A make-up foundation is prepared according to the invention by mixing the following ingredients:
partial glyceride of a fatty acid—9 g,
cetyl/stearyl alcohol ethoxylated with 10 mols of ethylene oxide—4 g,
paraffin oil—18 g,
polymer prepared according to Example 19—1 g,
magnesium/aluminum silicates—0.75 g,
anti-foam agent (Rhodorsil)—0.2 g,
methyl para-hydroxybenzoate—0.2 g,
softened water—66.85 g,
inorganic colorants—5 g.

In this Example, the polymer prepared according to Example 19 can be replaced by the same amount of one of the polymers prepared according to Examples 17 to 21, 26 and 28.

EXAMPLE O

A shampoo is prepared according to the invention by mixing the following ingredients:
copolymer obtained according to Example 50—0.1 g,
copolymer (90% vinyl acetate and 10% crotonic acid)—0.1 g,
sodium lauryl ether-sulphate (2.2 mols of ethylene oxide)—14 g,
lauric acid diethanolamide—3 g,
perfume—0.12 g,
dyestuff—0.2 g,
water, q.s.p.—100 g.

We claim:

1. A cosmetic composition to improve the suppleness and sheen of the hair and to facilitate the hydration and softness of the skin comprising a cosmetic vehicle suitable for application to the hair or skin and from 0.01 to 15% by weight of said composition of a polymer consisting essentially of recurring units of the formula:

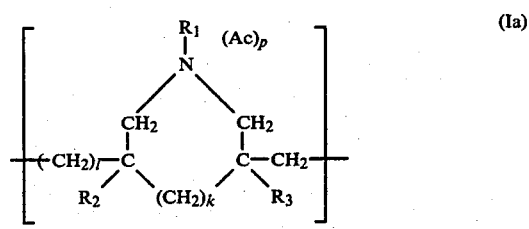

wherein:
k is 0 or 1, and l is 1 if k=0, or l is 0 if k=1,
p=0 or 1,
$R_2$ and $R_3$ each independently represent hydrogen or methyl,
$R_1$ represents a member selected from the group consisting of
(i) —$CH_2$—$COOR_6$ wherein $R_6$ represents alkyl having 1-3 carbon atoms,

(iv) —$(CH_2)_v$—CN wherein v is 1 or 2,
(v) —$COR_7$ wherein $R_7$ is selected from the group consisting of alkyl having 1-3 carbon atoms, —$CCl_3$, —$CH_2Cl$, phenyl and

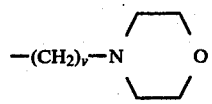

wherein v is 1 or 2,

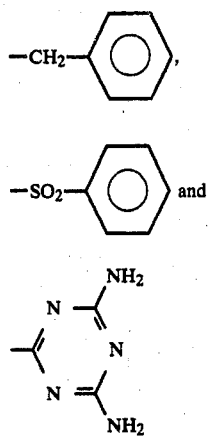 (vi)

(vii)

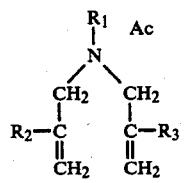 (viii)

and Ac if p is 1 is selected from the group consisting of hydrochloric acid, hydrobromic acid, nitric acid, acetic acid, butyric acid and lactic acid, said polymer having a molecular weight ranging from 2,000 to 500,000.

2. A cosmetic composition to improve the suppleness and sheen of the hair and to facilitate the hydration and softness of the skin comprising a cosmetic vehicle suitable for application to the hair or skin and from 0.01 to 15% by weight of said composition of a polymer consisting essentially of units derived from (1) 5 to 95 mol percent of a monomer having the formula:

$$\begin{array}{c} R_1 \quad Ac \\ | \\ N \\ / \quad \backslash \\ CH_2 \quad CH_2 \\ | \quad \quad | \\ R_2-C \quad \quad C-R_3 \\ \| \quad \quad \| \\ CH_2 \quad CH_2 \end{array} \quad \text{(XIII)}$$

wherein:

$R_2$ and $R_3$ each independently represent hydrogen or methyl, $R_1$ represents a radical selected from the group consisting of (i) —$CH_2$—$COOR_6$ wherein $R_6$ represents alkyl having 1-3 carbon atoms, (ii) —$CH_2$—$CH$—$CH_2Cl$,
         |
         OH (iii) —$CH_2$—CH—$CH_2$
              \ /
               O (iv) —$(CH_2)_v$—CN, wherein v is 1 or 2, (v) —$COR_7$ wherein $R_7$ is selected from the group consisting of alkyl having 1-3 carbon atoms, —$CCl_3$, —$CH_2Cl$, phenyl and —$(CH_2)_v$—N⟨  ⟩O, wherein v is 1 or 2,

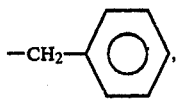 (vi)

(vii)

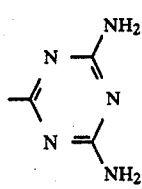 (viii)

and

Ac if p is 1 is selected from the group consisting of hydrochloric acid, hydrobromic acid, nitric acid, acetic acid, butyric acid and lactic acid, and (2) 5 to 95 mol percent of a monomer selected from the group consisting of (i) a monomer of the formula:

$$\begin{array}{c} R_8 \\ | \\ N \quad (Ac)_p \\ / \quad \backslash \\ H_2C \quad CH_2 \\ | \quad \quad | \\ R_2-C \quad \quad C-R_3 \\ \| \quad \quad \| \\ CH_2 \quad CH_2 \end{array} \quad \text{(IV)}$$

wherein:

$R_2$ and $R_3$ each independently represent hydrogen or methyl, $R_8$ represents a radical selected from the group consisting of —$CH_2$—$CH_2OH$ and —$(CH_2)_n$—$CH_3$ wherein n is 0 to 11, p is 0 or 1, and Ac if p is 1 represents an acid selected from the group consisting of hydrochloric acid, hydrobromic acid, nitric acid, acetic acid, butyric acid and lactic acid, (ii) a monomer of the formula:

$$\begin{array}{c} R_8 \quad \oplus \quad R_9 \quad A^\ominus \\ \backslash \quad N \quad / \\ / \quad \quad \backslash \\ H_2C \quad CH_2 \\ | \quad \quad | \\ R_2-C \quad \quad C-R_3 \\ \| \quad \quad \| \\ CH_2 \quad CH_2 \end{array} \quad \text{(V)}$$

wherein

A, $R_2$, $R_3$ and $R_8$ have the meaning given above, and $R_9$ represents methyl, (iii) a monomer of the formula:

$$CH_2=C-\overset{O}{\overset{\|}{C}}-O-R_{10} \quad \text{(VI)}$$
$\quad \quad |$
$\quad \quad R_{11}$ wherein $R_{11}$ represents hydrogen or methyl, $R_{10}$ represents a member selected from the group consisting of hydrogen, linear or branched alkyl having 1–18 carbon atoms, alkyl having 1–3 carbon atoms and substituted by alkoxy having 1–4 carbon atoms,

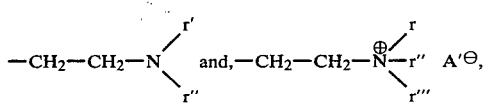

wherein r, r" r''' which may be identical or different represent alkyl having 1 to 4 carbon atoms, and A' represents Cl, Br, I or —OSO₃CH₃, (iv) a monomer of the formula:

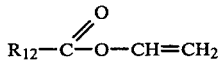   (VII)

wherein
R₁₂ represents linear or branched alkyl having 1–18 carbon atoms, (v) a monomer of the formula:

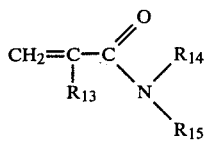   (VIII)

wherein
R₁₃ represents hydrogen or methyl, and R₁₄ and R₁₅ each independently represent a member selected from the group consisting of hydrogen, alkyl having 1–4 carbon atoms and alkyl having 1–4 carbon atoms and substituted by 1–3 hydroxy groups, and (vi) N-vinylpyrrolidone, said polymer having a molecular weight of 2,000 to 500,000.

3. A cosmetic composition to improve the suppleness and sheen of the hair and to facilitate the hydration and softness of the skin comprising a cosmetic vehicle suitable for application to the hair or skin and from 0.01 to 15% by weight of said composition of a polymer consisting essentially of units derived from (1) 50 to 95 mol percent of a monomer having the formula:

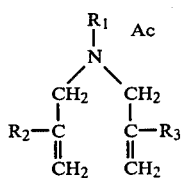   (XIII)

wherein
R₂ and R₃ each independently represent hydrogen or methyl,
R₁ represents a radical selected from the group consisting of
(i) —CH₂—COOR₆ wherein R₆ represents alkyl having 1–3 carbon atoms,

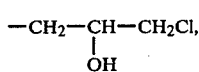   (ii)

-continued

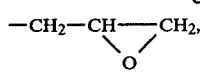   (iii)

(iv) —(CH₂)ᵥ—CN, wherein v is 1 or 2,
(v) —COR₇, wherein R₇ is selected from the group consisting of alkyl having 1–3 carbon atoms, —CCl₃, —CH₂Cl, phenyl and

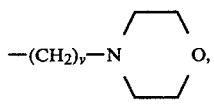

wherein v is 1 or 2,

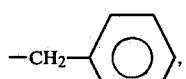   (vi)

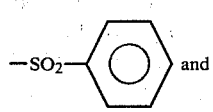   (vii)

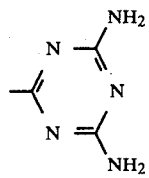   (viii)

and
Ac if p is 1 is selected from the group consisting of hydrochloric acid, hydrobromic acid, nitric acid, acetic acid, butyric acid, and lactic acid, and (2) 5 to 50 mol percent of a monomer selected from the group consisting of
(i) a monomer of the formula:

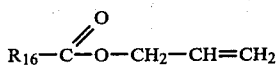   (X)

wherein
R₁₆ represents alkyl having 1–17 carbon atoms,
(ii) a monomer of the formula:

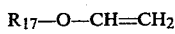   (XI)

wherein
R₁₇ represents alkyl having 1–18 carbon atoms and
(iii) a monomer of the formula:

wherein
R₁₈ represents alkyl having 1–18 carbon atoms, said polymer having a molecular weight ranging from 2,000 to 500,000.

4. The composition of claim 1 wherein the polymer has a molecular weight of 4,000 to 75,000.

5. The composition of claim 1 wherein the polymer is present in an amount of from 0.1 to 10% by weight.

6. The composition of claim 1 wherein the cosmetic vehicle is an aqueous or aqueous alcoholic solution, in which the alcohol is ethanol or isopropanol, said composition having a pH of 6 to 8 and constituting a hair treatment composition.

7. The composition of claim 1 wherein the cosmetic vehicle is an aqueous, alcoholic or aqueous alcoholic solution, the alcohol being ethanol or isopropanol, the amount of said copolymer present being from 0.1 to 5% by weight and constituting a wavesetting lotion.

8. The cosmetic composition of claim 1 wherein said recurring units are derived, by cyclopolymerization, from diallylamine selected from the group consisting of the hydrochloride, hydrobromide, nitrate, acetate, butyrate and lactate of N-trichloroacetyl-diallylamine, N-chloro acetyl diallylamine, N-acetonitrile-diallylamine, N-acetyl-diallylamine, N-propionitrile-diallylamine, N-propionyl-diallylamine, N-benzene-sulphonyl-diallylamine, N-ethyl acetate-diallylamine, N-methyl acetate diallylamine and the hydrochloride, hydrobromide, nitrate, acetate, butyrate and lactate of diallylmelamine.

* * * * *

UNITED STATES PATENT AND TRADEMARK OFFICE
CERTIFICATE OF CORRECTION

PATENT NO. : 4,426,375
DATED : January 17, 1984
INVENTOR(S) : Bernard JACQUET, et al It is certified that error appears in the above-identified patent and that said Letters Patent is hereby corrected as shown below:

IN THE HEADING:

At Section [62] entitled "RELATED U.S. APPLICATION DATA", correct the Pat. No. to read:

-- 4,287,172 --.

*Signed and Sealed this*

*Twenty-ninth* Day of *May 1984*

[SEAL]

*Attest:*

GERALD J. MOSSINGHOFF

*Attesting Officer* *Commissioner of Patents and Trademarks*